United States Patent [19]
Murthy et al.

[11] Patent Number: 6,132,286
[45] Date of Patent: Oct. 17, 2000

[54] PREPARATION OF 1,2,5,6-TETRA-HYDRO-3-CARBOALKOXYPRIDINES SUCH AS ARECOLINE AND SALTS OF 1,2,5,6-TETRAHYDRO-3-CARBOALKOXYPYRIDINES AND ARECOLINE HYDROBROMIDE

[75] Inventors: K. S. Keshave Murthy; Allan W. Rey, both of Brantford; Dan S. Matu, Mississauga, all of Canada

[73] Assignee: Brantford Chemicals Inc., Brantford, Canada

[21] Appl. No.: 08/914,271

[22] Filed: Aug. 19, 1997

[30] Foreign Application Priority Data

Aug. 7, 1997 [CA] Canada .................................. 2212449

[51] Int. Cl.$^7$ ................................................ C07D 211/74
[52] U.S. Cl. ........................................... 446/318; 546/319
[58] Field of Search ..................... 546/318, 319

[56] References Cited

PUBLICATIONS

Dobrowsky, A., A simple synthesis of arecoline, *Monaish*, 1952, vol. 83, pp. 443–447, together with English abstract;.
Kozello, I.A. et al., "Improvement of the Synthesis of Arecoline From Nicotinic Acid", *Khim. Farm. Zh.*, 1976, vol. 10, No. 11, pp. 90–91;.
Panouse, J.J., "Reduction of quaternary pyridinium salts with potassium borohydride. Application to the preparation of arecoline and determination of the structure of dihydro-codehydrases.", *C.R. Acad. Sci.* (*Paris*), 1951, v. 233, pp. 1200–1202;.
Lyle, R.E., et al., "Methyl 1–methyl–1,2,3,6–tetrahydroi-sonicotinate", *Journal of Organic Chemistry*, 1955, pp. 1761–1766;.
Gribble, G.W. et al., "Sodium Borohydride in Carboxylic Acid Media. A Review of the Synthetic Utility of Acyloxyborohydrides", *Organic Preparations and Procedures Int.*, 17, 1985, (4–5), pp. 317–384.

*Primary Examiner*—Jane Fan
*Attorney, Agent, or Firm*—Ivor M. Hughes; Neil H. Hughes; Marcelo K. Sarkis

[57] ABSTRACT

A process is provided for the preparation of 1,2,5,6-tetrahydro-3-carboalkoxypyridines of formula (III)

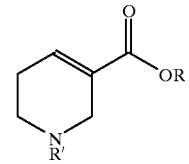

(III)

wherein R is a straight or cyclic substituted or unsubstituted alkyl chain having 1 to 6 carbon atoms, phenyl $C_{1-6}$ alkyl, menthol or a derivative of menthol, or a derivative of camphor, and R' is an alkyl chain having 1 to 4 carbon atoms or phenyl $C_{1-6}$ alkyl comprising reacting an alkyl pyridinium salt of formula

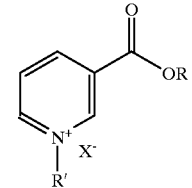

(II)

wherein R and R' are as defined above and X is a suitable leaving group with sodium triacetoxyborohydride in the presence of an acid.

19 Claims, No Drawings

PREPARATION OF 1,2,5,6-TETRA-HYDRO-3-CARBOALKOXYPRIDINES SUCH AS ARECOLINE AND SALTS OF 1,2,5,6-TETRAHYDRO-3-CARBOALKOXYPRIDINES AND ARECOLINE HYDROBROMIDE

FIELD OF INVENTION

This invention relates to improved processes for the manufacture of 1,2,5,6-tetrahydro-3-carboalkoxypyridines such as arecoline and salts of 1,2,5,6-tetrahydro-3-carboalkoxypyridines such as arecoline hydrobromide. Compounds of this type are also suitable intermediates for the manufacture of medicines such as paroxetine and femoxetine.

BACKGROUND OF THE INVENTION

Arecoline is a known cholinergic and anthelimitic agent. Arecoline itself has uses such as an anthelmintic and, especially by veterinarians, as an teniacide for dogs, cats, and poultry, cathartic in horses, and ruminatoric in cattle. Arecoline is also a suitable intermediate for the manufacture of medicaments such as paroxetine and femoxetine. It is obtained commercially by the extraction of betel nuts and is currently very expensive.

Several synthetic approaches have been reported for the production of arecoline. In the processes taught in "Ubereine einfache Arecolinsynthese", Monasche 1952, pp.443–447 and U.S. Pat. No. 2,506,458, the processes suffer from comprising many steps. Processes involving the borohydride reduction of methyl nicotinate methiodide ($KBH_4$ in neutral media, Khim. Farm. Zh., 1976, 10, pp. 90–91 and $KBH_4$ in an alkaline medium, C.R. Acad. Sci. (Paris), 1951, v. 233, pp.1200–1202) suffer from lower yield, high levels of impurities, and difficulties in scale-up. The use of $NaBH_4$ in a methanol medium gives a low yield (36%) of arecoline (Journal of Organic Chemistry, pp. 1761–1766, 1955). Upon scale-up, the yields would be further diminished due to competing saponification during the aqueous extractive work-up. Another disadvantage is that these processes evolve large amount of the explosive gas hydrogen.

SUMMARY OF THE INVENTION

According to one aspect of this invention, an improved process for making 1,2,5,6-tetrahydro-3-carboalkoxypyridine compounds (ie., formula III in Scheme 1) was developed which comprises of reacting an alkyl pyridinium salt (formula II, Scheme 1) with sodium triacetoxyborohydride in the presence of an acid thereby avoiding the difficulties mentioned above. According to another aspect of this invention the improved process may comprise reacting the less expensive sodium borohydride in the presence of acetic acid thereby generating, in situ, sodium triacetoxyborohydride (Organic Preparations and Procedures Int., 17, (4–5), pp. 317–384). Quite unexpectedly, we noted that for the novel reduction of this type, the yield was increased from 36–42% to 55–60%.

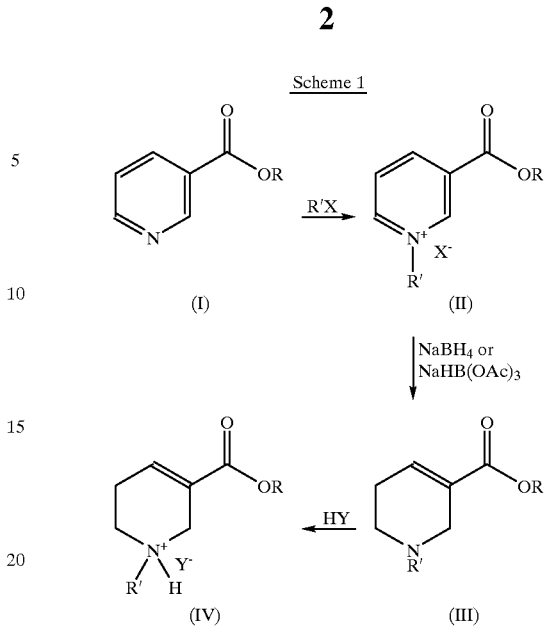

Scheme 1

The pyridine compound (I) where R is a straight or cyclic substituted or unsubstituted alkyl chain having 1 to 6 carbon atoms, phenyl $C_{1-6}$ alkyl, menthol or a derivative of menthol, or a derivative of camphor, most preferably R is methyl, may be an intermediate used to manufacture compound II. In this regard compound I is dissolved in an organic solvent for the reaction (alkylation). The identity of the solvent is not particularly critical so long as it does not interfere with the intended alkylation reaction, and is not reactive with the starting materials or products formed. Suitable solvents include halogenated hydrocarbons, esters, ethers, nitrites, and the like. Suitable solvents include ethyl acetate, n-propyl acetate, heptane, tetrahydrofuran, t-butyl methyl ether, acetonitrile, methyl ethyl ketone, methyl isobutyketone, or acetone or combinations thereof. The most preferable solvents are acetone and heptane. The pyridine compound (I) may be alkylated with typically 0.9 to 1.5 equivalents of an alkylating agent, R'X, where R' is an alkyl chain having 1 to 4 carbon atoms or phenyl $C_{1-6}$ alkyl, most preferably R' is methyl and X is a leaving group such as a halide or tosylate, most preferably X is iodide. The alkyl pyridinium salt (II) produced is dissolved in a lower alcohol, for instance methanol, ethanol, propanol, butanol or water or combinations thereof. The most preferable solvent is methanol. To this media is added an acid for example acetic acid (4–12 equivalents) followed by sodium triacetoxyborohydride (3–4 equivalents) or sodium borohydride (2–3 equivalents). To the flask is added water and the reaction mixture neutralized using a base such as sodium hydroxide or potassium hydroxide producing the 1,2,5,6-tetrahydro-3-carboalkoxypyridine compound (III). Compound III may be extracted using an organic solvent such as n-butanol or toluene. The free amine may be isolated at this stage or converted into a salt by contact with an acid, HY. Examples of Y include bromide, chloride, iodide, acetate, maleate, tartrate, most preferably bromide. These salts are conveniently isolated by concentration of the organic solvent until precipitation and collected by filtration.

The following examples are illustrative of the invention and are not to be construed as limiting the scope of the invention in any manner.

EXAMPLE 1

Preparation of methyl nicotinate methiodide (Formula II, Scheme 1, where R'=R=Me, X=I⁻)

A round bottom flask is charged with methyl nicotinate (274.28 g, 2.0 mol) and acetone (1.37 L) followed by iodomethane (255.49 g, 1.8 mol, 0.9 eq). This mixture is stirred and heated to 35–40° C. for 24 hours. The mixture is then cooled to 20–25° C. and charged with heptane (1.37 L) and stirred and cooled to 5° C. and maintained at this temperature for 1 hour. The methyl nicotinate methiodide is collected by Buchner filtration and the filter cake is rinsed with a 1:1 (v/v) heptane/acetone mixture and dried at 40–45° C. in a vacuum oven for 12 hours.

This provided 477.7 g (95% yield) of methyl nicotinate methiodide. mp. 132.6–136.3° C.; $^1$H NMR ($D_2O$, 300 MHZ), d=9.41 (s, 1H), 9.01 (d, J=7.5 Hz, 1H), 8.98 (d, J=4.5 Hz, 1H), 8.18 (t, J=7.0 Hz), 4.45 (s, 3H), 4.02 (s, 3H).

EXAMPLE 2

Preparation of arecoline free base using sodium borohydride (Formula III, Scheme 1, where R'=R=Me)

To a flask equipped with a mechanical stirrer and thermometer is added methyl nicotinate methiodide (250 g, 0.895 mol), methanol (2.5 L), and acetic acid (430.3 g, 7.16 mol, 8 eq.). The flask is cooled to 0° C. at which point sodium borohydride pellets (67.79 g, 1.79 mol, 2 eq.) are added in 10 equal additions over a 2 hour period. The temperature is maintained below 10° C. throughout the addition. The cooling bath is removed and the mixture allowed to warm to room temperature. Water is added (0.25 L) while keeping the temperature at <10° C. The flask is warmed to room temperature and then the volatiles are removed to a final volume of 1.0 L at which point water is added and the aqueous mixture washed twice with toluene. To the aqueous layer is added toluene and the biphasic mixture cooled to 5° C. and the pH adjusted from 4.40 to 10.10 by addition of sodium hydroxide while maintaining the temperature below 20° C. The layers are separated and the aqueous layer re-extracted with toluene and the combined toluene layers are washed with brine, concentrated to 250 mL, cooled to 5° C., and filtered through Celite. Subsequent concentration to 250 mL (weight=314.5 g) and assay demonstrated a composition of 75.6 g of arecoline free base (55% yield) with the remainder being toluene. $^1$H NMR ($CDCl_3$, 300 MHz), d=6.99 (s, 1H), 3.72 (s, 3H), 3.14 (d, J=2.2 Hz, 1H), 2.47 (t, J=5.5 Hz, 2H), 2.39 (s, 3H), 2.33 (m, 2H).

EXAMPLE 3

Preparation of arecoline hydrobromide using sodium triacetoxyborohydride (Formula IV, Scheme 1, where R'=R=Me, Y=Br$^-$)

To a flask equipped with a mechanical stirrer and thermometer is added methyl nicotinate methiodide (111.63 g, 0.40 mol), methanol (1.11 L), and acetic acid (192 g, 3.2 mol, 8 eq). Sodium triacetoxyborohydride (372.06 g, 1.6 mol, 4 eq) is added in 8 equal portions at 23° C. After each addition, the temperature increases to 28° C. and the reaction mixture is allowed to recool to 23° C. before the next addition. After all the borohydride reagent has been added, the mixture is stirred a further 2 hours at which point water is added (111.6 g) over a 30 min period while keeping the temperature at 20° C. The reaction mixture is concentrated to 650 mL and then charged with additional water and stirred until all the salts are dissolved. The pH is then adjusted form pH 4.3 to 9.6 using 25% sodium hydroxide while maintaining the temperature at <20° C. The mixture is then extracted with n-butanol and the combined n-butanol extracts are evaporated to 487 g. The KF at this point is 0.43%. The mixture is treated with charcoal for 30 min, filtered through Celite, and the Celite pad is rinsed with n-butanol. The filtrate is cooled to 10° C. and acidified to a pH of 0.63 using 48% hydrobromic acid while keeping the temperature between 10 and 15° C. The mixture is concentrated to a volume of 150 mL, cooled to 5° C., and the precipitated arecoline hydrobromide is filtered off and rinsed with n-butanol and ethyl acetate, and the product dried at 45° C. in a vacuum oven to provide 44.35 g (47.0% yield) of arecoline hydrobromide. mp. 170.6–171.9° C.; H NMR ($D_2O$, 300 MHz), d=7.18 (septet, J=1.9 Hz, 1H), 4.15 (d, J=15.1 Hz, 1H), 3.80 (br. s, 1H), 3.76 (s, 3H), 3.54 (m, 1H), 3.21 (m, 1H), 2.97 (s, 3H), 2.67 (m, 2H).

EXAMPLE 4

Preparation of arecoline hydrobromide using sodium borohydride (Formula IV, Scheme 1, where R'=R=Me, Y=Br$^-$)

To a flask equipped with a mechanical stirrer and thermometer is added methyl nicotinate methiodide (83.7 g, 0.30 mol), methanol (0.837 L), and acetic acid (216 g, 3.6 mol, 12 eq.). The flask is cooled to −5° C. at which point sodium borohydride pellets (23.16 g, 0.6 mol, 2 eq.) are added in 10 equal additions over a 2 hour period. The temperature is maintained at −5° C. to 0C. The cooling bath is removed and the mixture allowed to warm to room temperature and stirred a further 3 hours. The reaction mixture is recooled to 5° C. whereupon water is added over a 30 min period while keeping the temperature at <10C. The pH is adjusted from pH 4.5 to 9.7 using 25% sodium hydroxide while maintaining the temperature at <10° C. The mixture is then extracted with toluene and the combined toluene layers washed with water. The arecoline free base may be used at this point or converted to the hydrobromide salt by adding 50 mL of water followed by 48% hydrobromic acid (37.25 g, 0.22 mol). The toluene layer is re-extracted with water and the combined aqueous layers treated with charcoal. The charcoal is removed by Celite filtration and the Celite pad is rinsed with water. The filtrate is co-evaporated with n-butanol (500 mL) to a final volume of 150 mL and the precipitated arecoline hydrobromide is filtered off and rinsed with n-butanol and ethyl acetate and the product dried at 45° C. in a vacuum oven to provide 30.7 g (43.3% yield) of arecoline hydrobromide.

As many changes can be made to the embodiments without departing from the scope of the invention, it is intended that all material be interpreted as illustrative of the invention and not in a limiting sense.

What is claimed is:

1. A process for the preparation of 1,2,5,6-tetrahydro-3-carboalkoxypyridines of formula (III)

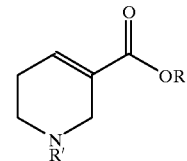

(III)

wherein R is a straight or cyclic substituted or unsubstituted alkyl chain having 1 to 6 carbon atoms, phenyl $C_{1-6}$ alkyl, menthol or a derivative of menthol, or a derivative of camphor, and R' is an alkyl chain having 1 to 4 carbon atoms or phenyl $C_{1-6}$ alkyl comprising reacting an alkyl pyridinium salt of formula (II)

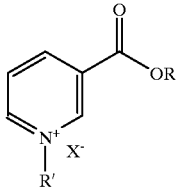

(II)

wherein R and R' are as defined above and X is a suitable leaving group with sodium triacetoxyborohydride in the presence of an acid.

2. A process for the preparation of 1,2,5,6-tetrahydro-3-carboalkoxypyridines of formula (III)

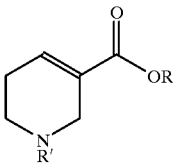

(III)

wherein R is a straight or cyclic substituted or unsubstituted alkyl chain having 1 to 6 carbon atoms, phenyl $C_{1-6}$ alkyl, menthol or a derivative of menthol, or a derivative of camphor, and R' is an alkyl chain having 1 to 4 carbon atoms or phenyl $C_{1-6}$ alkyl comprising reacting an alkyl pyridinium salt of formula (II)

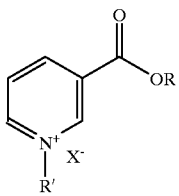

(II)

wherein R and R' are as defined above and X is a suitable leaving group with sodium borohydride in the presence of acetic acid.

3. A process for the preparation of salts of 1,2,5,6-tetrahydro-3-carboalkoxypyridines of formula (IV)

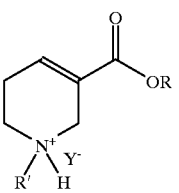

(IV)

wherein R is a straight or cyclic substituted or unsubstituted alkyl chain having 1 to 6 carbon atoms, phenyl $C_{1-6}$ alkyl, menthol or a derivative of menthol, or a derivative of camphor, and R' is an alkyl chain having 1 to 4 carbon atoms or phenyl $C_{1-6}$ alkyl and Y is selected from bromide, chloride, iodide, acetate, maleate, tartrate comprising reacting an alkyl pyridinium salt of formula (II)

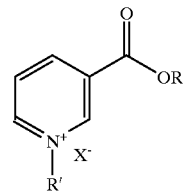

(II)

wherein R and R' are as defined above and X is a suitable leaving group with sodium triacetoxyborohydride in the presence of an acid followed by reacting with an acid, HY, wherein Y is as defined above.

4. A process for the preparation of salts of 1,2,5,6-tetrahydro-3-carboalkoxypyridines of formula (IV)

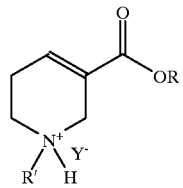

(IV)

wherein R is a straight or cyclic substituted or unsubstituted alkyl chain having 1 to 6 carbon atoms, phenyl $C_{1-6}$ alkyl, menthol or a derivative of menthol, or a derivative of camphor, and R' is an alkyl chain having 1 to 4 carbon atoms or phenyl $C_{1-6}$ alkyl and Y is selected from bromide, chloride, iodide, acetate, maleate, tartrate comprising reacting an alkyl pyridinium salt of formula (II)

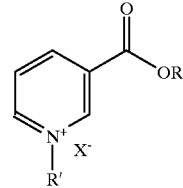

(II)

wherein R and R' are as defined above and X is a suitable leaving group with sodium borohydride in the presence of an acid followed by reacting with an acid, HY, wherein Y is as defined above.

5. A process for the preparation of arecoline (formula III, where R=R'=Me)

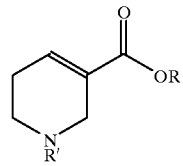

(III)

comprising reacting methyl nicotinate methylhalide (formula II where R=R'=Me and X is selected from Cl⁻, Br⁻, I⁻)

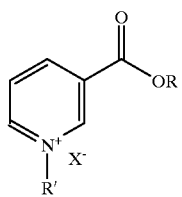
(II)

with sodium triacetoxyborohydride in the presence of an acid.

6. A process for the preparation of arecoline (formula III, where R=R'=Me)

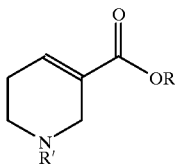
(III)

comprising reacting methyl nicotinate methiodide (formula II where R=R'=Me and X=I⁻)

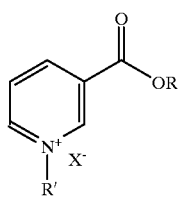
(II)

with sodium triacetoxyborohydride in the presence of an acid.

7. A process for the preparation of arecoline hydrobromide (formula IV where R=R'=Me and Y=Br⁻)

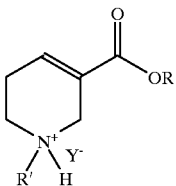
(IV)

comprising reacting methyl nicotinate methylhalide (formula II where R=R'=Me and X is selected from Cl⁻, Br⁻, I⁻)

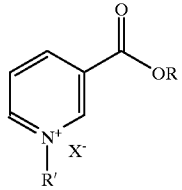
(II)

with sodium triacetoxyborohydride in the presence of an acid followed by reacting with hydrobromic acid.

8. A process for the preparation of arecoline hydrobromide (formula IV where R=R'=Me and Y=Br⁻)

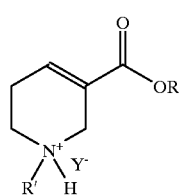
(IV)

comprising reacting methyl nicotinate methiodide (formula II where R=R'=Me and X=I⁻)

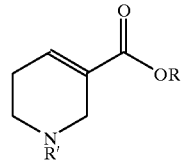
(II)

with sodium triacetoxyborohydride in the presence of an acid followed by reacting with hydrobromic acid.

9. A process for the preparation of arecoline (formula III, where R=R'=Me)

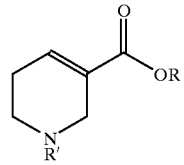
(III)

comprising reacting methyl nicotinate methylhalide (formula II where R=R'=Me and X is selected from Cl⁻, Br⁻, I⁻)

(II)

with sodium borohydride in the presence of acetic acid.

10. A process for the preparation of arecoline (formula III, where R=R'=Me)

(III)

comprising reacting methyl nicotinate methiodide (formula II where R=R'=Me and X=I⁻)

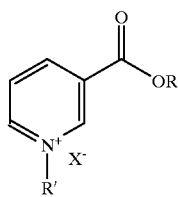

(II)

with sodium borohydride in the presence of acetic acid.

11. A process for the preparation of arecoline hydrobromide (formula IV where R=R'=Me and Y=Br⁻)

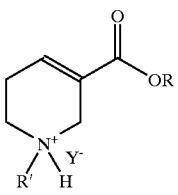

(IV)

comprising reacting methyl nicotinate methylhalide (formula II where R=R'=Me and X is selected from Cl⁻, Br⁻, I⁻)

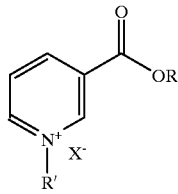

(II)

with sodium borohydride in the presence of acetic acid followed by reacting with hydrobromic acid.

12. A process for the preparation of arecoline hydrobromide (formula IV where R=R'=Me and Y=Br⁻)

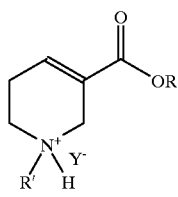

(IV)

comprising reacting methyl nicotinate methiodide (formula II where R=R'=Me and X=I⁻)

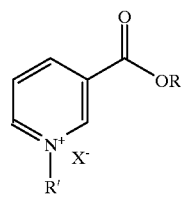

(II)

with sodium borohydride in the presence of acetic acid followed by reacting with hydrobromic acid.

13. A process for the transformation of alkyl pyridinium salts into 1,2,5,6-tetrahydro-3-carboalkoxypyridine heterocycles by contact of the alkyl pyridinium salt with borohydride reducing agents of structure $MBH_4$ where M is sodium, lithium, potassium in an acetic acid.

14. A process for the transformation of alkyl pyridinium salts into 1,2,5,6-tetrahydro-3-carboalkoxypyridine heterocycles by contact of the alkyl pyridinium salt with sodium borohydride in an acetic acid.

15. A process for the transformation of alkyl pyridinium salts into 1,2,5,6-tetrahydro-3-carboalkoxypyridine heterocycles by contact of the alkyl pyridinium salt with borohydride reducing agents of structure $MBH(CH_3COOH)_3$ where M is sodium, lithium, potassium in an acidic media.

16. A process for the transformation of alkyl pyridinium salts into 1,2,5,6-tetrahydro-3-carboalkoxypyridine heterocycles by contact of the alkyl pyridinium salt with sodium triacetoxyborohydride in an acidic media.

17. The process of claims 1, 2, 3 or 4 where R is Methyl.

18. The process of claims 1, 3, 5, 6, 7, 8, 15 or 16 wherein the acid is acetic acid.

19. The process of claim 17 wherein the acid is acetic acid.

* * * * *